United States Patent
Pan et al.

(10) Patent No.: US 9,669,215 B2
(45) Date of Patent: Jun. 6, 2017

(54) MEDICAL ELECTRONIC DEVICE

(71) Applicant: GiMer Medical Co., Ltd., New Taipei (TW)

(72) Inventors: Jian-Hao Pan, New Taipei (TW); Chi-Heng Chang, New Taipei (TW)

(73) Assignee: Gimer Medical Co., Ltd., New Taipei (TW)

( * ) Notice: Subject to any disclaimer, the term of this patent is extended or adjusted under 35 U.S.C. 154(b) by 0 days.

(21) Appl. No.: 14/873,032

(22) Filed: Oct. 1, 2015

(65) Prior Publication Data
US 2016/0096023 A1   Apr. 7, 2016

(30) Foreign Application Priority Data

Oct. 1, 2014   (TW) .............................. 103217436 U

(51) Int. Cl.
| | | |
|---|---|---|
| *A61N 1/00* | (2006.01) | |
| *A61N 1/36* | (2006.01) | |
| *A61N 1/378* | (2006.01) | |
| *A61N 1/05* | (2006.01) | |
| *A61N 1/372* | (2006.01) | |
| *H02J 7/02* | (2016.01) | |
| *H02J 7/04* | (2006.01) | |
| *A61N 1/34* | (2006.01) | |

(52) U.S. Cl.
CPC ....... *A61N 1/36071* (2013.01); *A61N 1/0551* (2013.01); *A61N 1/36021* (2013.01); *A61N 1/378* (2013.01); *A61N 1/3787* (2013.01); *A61N 1/37247* (2013.01); *H02J 7/025* (2013.01); *H02J 7/04* (2013.01); *A61N 2001/34* (2013.01)

(58) Field of Classification Search
CPC .............. A61N 1/36071; A61N 1/0551; A61N 1/36021; A61N 1/37247
USPC ........................................................... 607/46
See application file for complete search history.

(56) References Cited

U.S. PATENT DOCUMENTS

| | | | | |
|---|---|---|---|---|
| 6,246,912 B1* | 6/2001 | Sluijter | .............. | A61N 1/36017 607/100 |
| 2013/0317564 A1 | 11/2013 | Lin et al. | | |
| 2014/0070761 A1* | 3/2014 | Labbe | .................... | A61N 1/378 320/108 |

FOREIGN PATENT DOCUMENTS

EP         2705877 A1    3/2014

* cited by examiner

*Primary Examiner* — Amanda Patton
*Assistant Examiner* — Philip C Edwards
(74) *Attorney, Agent, or Firm* — Muncy, Geissler, Olds & Lowe, P.C.

(57) ABSTRACT

A medical electronic device comprises at least a battery module, a detector for detecting the remaining battery of the battery module to generate a detection signal, a processor generating a first status information according to the detection signal, a transceiver and a function circuit. The processor transmits and receives the first status information and the control signal by the transceiver. The function circuit is electrically connected to the processor and at least an electrode. The electrode extends outward from the medical electronic device. According to the control signal, the processor controls the function circuit to output an electrical stimulation signal with default stimulation frequency, stimulation cycle and stimulation intensity to the electrode. The voltage of the electrical stimulation signal ranges from −10V to −1V and from 1V to 10V, and the frequency of the electrical stimulation signal is between 200 KHz and 800 KHz.

13 Claims, 2 Drawing Sheets

MEDICAL ELECTRONIC DEVICE

CROSS REFERENCE TO RELATED APPLICATIONS

This Non-provisional application claims priority under 35 U.S.C. §119(a) on Patent Application No(s). 103217436 filed in Taiwan, Republic of China on Oct. 1, 2014, the entire contents of which are hereby incorporated by reference.

BACKGROUND

Technical Field

The invention relates to a medical electronic device, in particular to a medical electronic device which can be implanted into an organism and adjust the cycle day and intensity of the electrical stimulation on its own.

Related Art

Human nerve acts as paths for transmitting the instruction (current) issued from brain. Normally, human nerve has a threshold which is lower at the damaged nerve region. Thus, the person easily feels uncomfortable ache at the portion of the human body relating to the damaged nerve region so as to cause a chronic pain if the situation continues.

As the precision micro process becomes good enough to implant micro medical device in the human body, the develop of the researchers over the past few decades in this field earns recognition for clinical applications of the implantable medical device, for example, active implantable medical device (e.g. implantable electrical neurostimulator, glucose sensor or pacemakers, etc.).

U.S. Pat. No. 6,246,912 "Modulated high frequency tissue modification" discloses that a ground reference pad and an electrode shaft are respectively coupled to a pulsed high frequency generator, the electrode shaft is inserted into the patient's body and the electrode tip of the electrode shaft is located at the affected nerve, and the ground reference pad is placed on the external of the patient's body to complete an electrical circuit through the patient's body. By the pulsed high frequency generator to generate a voltage output with a modulated high frequency waveform for example modulated burst radiofrequency waves, the electrode is driven to stimulate the affected nerve but it inhibits temperature elevation to the lethal temperature range of the tissue.

However, as to U.S. Pat. No. 6,246,912, the user is required to accurately and precisely control the pulse interval for effectively controlling the voltage output with the modulated high frequency waveform and inhibiting temperature elevation. Besides, one electrical stimulation for the patient relieves the pain in his affected nerve about several days, and conventional nerve electrical stimulator is configured with a default electrical stimulation cycle. For example, the conventional nerve electrical stimulator is configured to perform the electrical stimulation for a certain time period every day. Although the electrical stimulation every day can relieve the pain in the affected nerve of the patient, the threshold of the affected nerve becomes lower if the affected nerve is frequently electrically stimulated. As a result, the intensity of the electrical stimulation needs to be more intensive to effectively relieve the pain in the affected nerve.

SUMMARY

An aspect of the disclosure is to provide a medical electronic device which adjusts the cycle day and intensity of its electrical stimulation on its own depending on the habitual behavior of the user or patient (for example: cycle days of pain).

A medical electronic device comprises at least a battery module, a detector, a processor, a transceiver and a function circuit. The detector is electrically connected to the battery module and detects the remaining battery of the battery module to generate a detection signal. The processor is electrically connected to the detector to receive the detection signal and generate a first status information according to the detection signal, and receives at least a control signal. The transceiver is electrically connected to the processor. The processor transmits and receives the first status information and the control signal by the transceiver. The function circuit is electrically connected to the processor and at least an electrode. The electrode extends outward from the medical electronic device. According to the control signal, the processor controls the function circuit to output an electrical stimulation signal with default stimulation frequency, stimulation cycle and stimulation intensity to the electrode. The voltage of the electrical stimulation signal ranges from $-10V$ to $-1V$ and from $1V$ to $10V$, and the frequency of the electrical stimulation signal is between 200 KHz and 800 KHz.

In one embodiment, the medical electronic device further comprises a heat sensor. The heat sensor is electrically connected to the processor and monitors a temperature of the medical electronic device to generate a sensor signal to the processor. The processor generates a second status information according to the sensor signal.

In one embodiment, the battery module is a non-rechargeable battery.

In one embodiment, the medical electronic device further comprises an induction coil and a rectifier. The battery module is a rechargeable battery. The induction coil is induced by an AC magnetic field caused by an external charging device. The rectifier is electrically connected to the induction coil and the battery module to convert the current in the induction coil induced by the AC magnetic field into a DC current and transmit it to the battery module.

In one embodiment, the transceiver is linked to an external control device with wireless communication, the external control device has a plurality of setup keys and at least a screen, the external control device sends the control signal to the transceiver, and the processor receives the control signal by the transceiver.

In one embodiment, the transceiver is linked to an external control device with wireless communication, the external control device has a plurality of setup keys and at least a screen, the external control device sends the control signal to the transceiver, and the processor receives the control signal by the transceiver.

In one embodiment, the voltage of the electrical stimulation signal ranges from $-10V$ to $-3V$ and from $3V$ to $10V$.

In one embodiment, the interval between the electrode and at least one dorsal root ganglion of a human body is smaller than 2 cm to electrically stimulate the dorsal root ganglion.

In summary, the medical electronic device has a detector, a processor, a transceiver and a function circuit. The processor can receive at least a control signal, which has been set by default externally, and instruct the function circuit to output an electrical stimulation signal to the electrode according to the control signal. Because the electrical stimulation signal carries the information about the default electrical stimulation frequency, the default electrical stimulation cycle and the default electrical stimulation intensity, the medical electronic device can turn itself on according to the electrical stimulation signal for electrical stimulation depending on the habitual behavior of the user or patient (for example: cycle days of pain). Therefore, it can avoid less effective treatment due to frequently electrically stimulating the affected nerve of the patient like the conventional manner.

Moreover, because the medical electronic device has the detector, the remaining battery of the battery module can be instantly detected by the detector so as to as effective as possible monitor the operation of the medical electronic device.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

Figure 1:
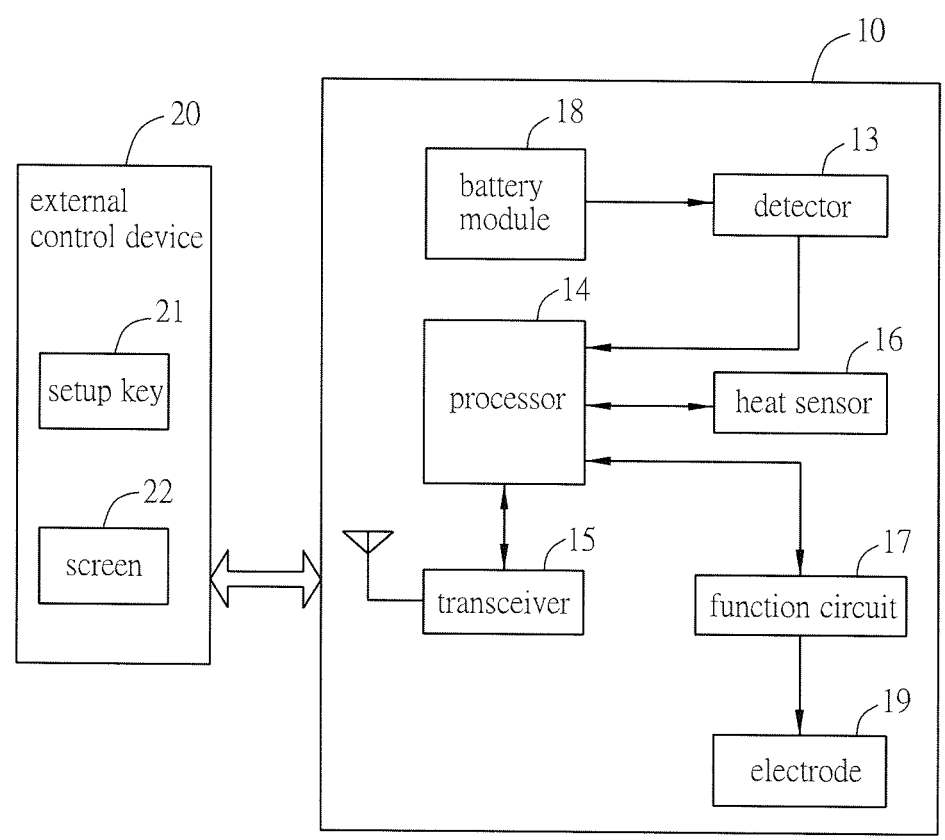
FIG. 1 is a block diagram of the medical electronic device according to the first embodiment.

Referring to FIG. 1, it is a block diagram of the medical electronic device according to the first embodiment. The medical electronic device 10 is adapted to be implanted in the individual. The medical electronic device 10 is preferably a device for stimulating nerve but it is not limited thereto. The medical electronic device 10 can set the parameters for electrical stimulation by an external control device 20. In the embodiment, the individual preferably is an organism, and it may include mammals such as mouse, human, rabbit, cattle, sheep, pig, monkey, dog, cat, etc. Preferably, it is human.

The medical electronic device 10 comprises a detector 13, a processor 14, a transceiver 15, a heat sensor 16, a function circuit 17, at least a battery module 18 and at least an electrode 19.

The detector 13 is electrically connected to the battery module 18. In the embodiment, the detector 13 is a battery fuel gauge, the detector 13 detects the remaining battery of the battery module 18 to output a detection signal to the processor 14. In the embodiment, the battery module 18 is a non-rechargeable battery, for example, Li-ion battery, Nickel-Zinc battery or fuel cell, etc., and it may be any battery which satisfies dimension and power requirements.

The processor 14 is electrically connected to the detector 13, the processor 14 receives the detection signal from the detector 13 and generates a first status information according to the detection signal. Besides, the processor 14 receives at least a control signal sent from the external control device 20. The control signal carries, for example but not limited to, instructions for inputting the electrical stimulation parameter, instructions for reading the electrical stimulation parameter, or instructions for executing the function circuit.

The transceiver 15 is electrically connected to the processor 14. The processor 14 can transmit the first status information by the transceiver 15 and also can receive the control signal by the transceiver 15.

The heat sensor 16 is electrically connected to the processor 14, and monitors a temperature of the medical electronic device 10 to generate a sensor signal to the processor 14. The processor 14 similarly transmits the sensor signal by the transceiver 15.

The function circuit 17 is electrically connected to the processor 14. The function circuit 17 is for example but not limited to a circuit for electrically stimulating nerve, it also may be a pacemaker, a cochlear implant, a visual prosthesis or a circuit for monitoring physiological signal. The function circuit 17 is electrically connected to at least an electrode 19, but the manner for disposing the electrode 19 is not limited. For example, the electrode 19 can be disposed outside the medical electronic device 10. The processor 14 receives the control signal sent from the external control device 20 and instructs the function circuit 17 to output an electrical stimulation signal to the electrode 19 according to the control signal. The electrical stimulation signal may carry the information about the default electrical stimulation frequency, the default electrical stimulation cycle and the default electrical stimulation intensity which preferably are adequate parameters having been tested and estimated by medical staffs during implantation.

After the processor 14 receives the detection signal from the detector 13, it generates the first status information according to the detection signal. Similarly, after the processor 14 also receives the sensor signal from the heat sensor 16, it generates a second status information according to the sensor signal. In the embodiment for example, the first status information indicates the remaining battery of the battery module 18 detected by the detector 13, and the second status information indicates the temperature of the medical electronic device 10 sensed by the heat sensor 16. Accordingly, the processor 14 receives the first status information and the second status information, and returns them to the external control device 20 by the transceiver 15 with wireless communication.

The external control device 20 is equipped with a plurality of setup keys 21 and the screen 22 for displaying status information and control information. After setting up by setup keys 21, the external control device 20 can send at least a control signal. In the embodiment, the control signal may carry information about the frequency, the stimulation cycle, the number of times, and the intensity, etc. for the electrical stimulation. Moreover, because the external control device 20 is linked to the transceiver 15 of the medical electronic device 10 with wireless communication, the first status information and the second status information received by the processor 14 return the external control device 20 by the transceiver 15 with wireless communication. The first status information and the second status information can be displayed on the screen 22 to illustrate the status of the medical electronic device 10 during electrical stimulation for the user or the medical staff who can adjust the input parameters according to the information.

Furthermore, after the processor 14 of the medical electronic device 10 receives the control signal sent from the external control device 20 by the transceiver 15, it can instruct the function circuit 17 by the processor 14 to output an electrical stimulation signal to the electrode 19 according to the cycle day for the electrical stimulation, the number of times for the electrical stimulation, or the intensity for the electrical stimulation which have been set in the control signal. For example, the cycle day for the electrical stimulation is set to every three days to initial the electrical stimulation. As a result, the medical electronic device 10 turns itself on every few days depending on the habitual behavior of the user or patient (for example: cycle days of pain), and adjusts the frequency, the stimulation cycle and the intensity for the electrical stimulation provided by the medical electronic device 10 on its own. It prevents the patient from excessive electrical stimulation on the affected nerve and thus avoids less effective treatment.

In implementation, the voltage of the electrical stimulation signal ranges from −10V to −1V and from 1V to 10V, and its frequency is between 200 KHz and 800 KHz. Preferably, the voltage of the electrical stimulation signal ranges from −10V to −3V and from 3V to 10V and its frequency is also between 200 KHz and 800 KHz.

While applying the medical electronic device 10 in the embodiment to a human body, the processor 14 controls the function circuit 17 to transmits the electrical stimulation signal to the electrode 19 so as to keep an interval between the electrode 19 and the dorsal root ganglion of the human body. Preferably, the interval is smaller than 2 cm to stimulate the dorsal root ganglion with the electrical stimulation of low intensity, low temperature, and high frequency. It damages as little as possible the nerve tissue of the dorsal root ganglion, but still inhabit biomolecule generation in the dorsal root ganglion and raise the threshold of the electrical stimulated dorsal root ganglion so as to lower the neurotransmission capability in the electrically stimulated dorsal root ganglion and reduce the nerve pain of the patient as much as possible.

Figure 2:
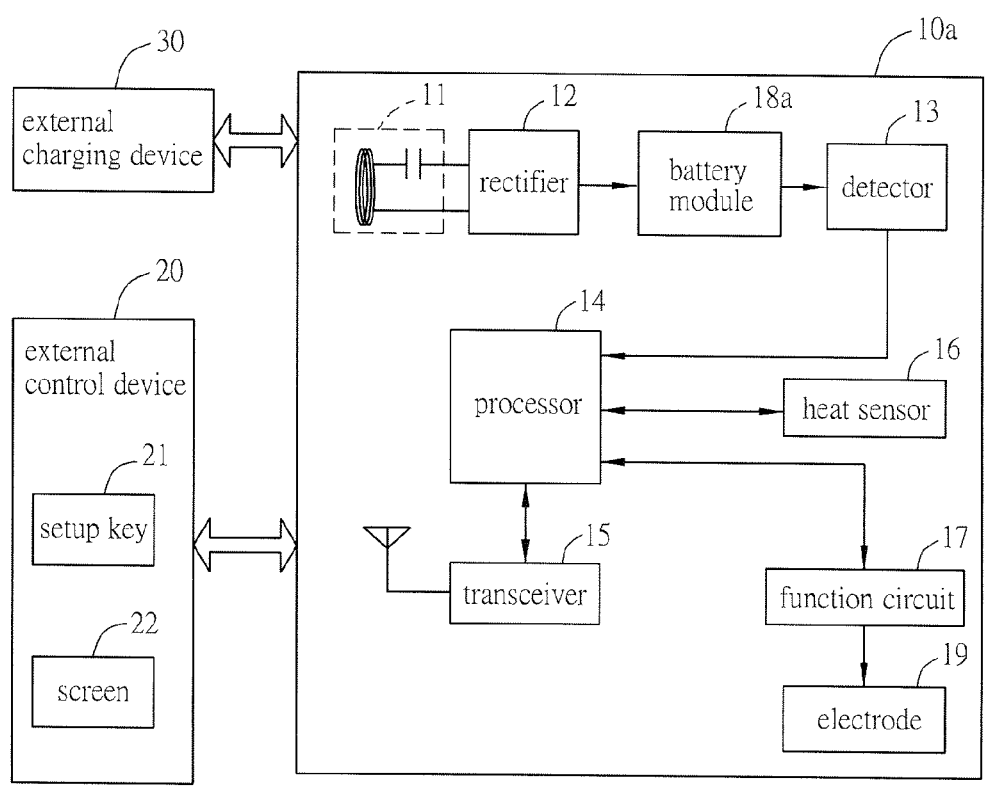
FIG. 2 is a block diagram of the medical electronic device according to the second embodiment.

Another medical electronic device 10a is shown in FIG. 2. FIG. 2 is a block diagram of the medical electronic device according to the second embodiment. The medical electronic device 10a in the embodiment and the medical electronic device 10 in the previous embodiment have similar structures. But the medical electronic device 10a can be charged by a default external charging device 30. In the embodiment, the battery module 18a is a rechargeable battery, and the medical electronic device 10a further comprises an induction coil 11 and a rectifier 12. The induction coil 11 is induced by AC magnetic field which is generated by the external charging device 30. The rectifier 12 is electrically connected between the induction coil 11 and the battery module 18a to convert the current in the induction coil 11 induced by the AC magnetic field into a DC current, and then transmits it to the battery module 18a.

Furthermore, the external charging device 30 can produce the AC magnetic field covering the medical electronic device 10a, so the induction coil 11 of the medical electronic device 10a is induced by the AC magnetic field and then the rectifier 12 converts the current induced by AC magnetic field into a DC current and outputs it to the battery module 18a so as to wirelessly charge the medical electronic device 10.

For example, when the battery module 18a is being charged, the detector 13 also can detect the remaining battery of the battery module 18a to generate a detection signal. For example, an additional voltage detector (not shown in the figure) may be provided, or the voltage detector is integrated into the processor 14 to detect the charging voltage.

As mentioned above, after receiving the detection signal, the processor 14 generates the first status information according to the detection signal. The first status information may indicate the remaining battery of the battery module 18 detected by the detector 13, and then the processor 14 wirelessly sends the first status information to the external control device 20 by the transceiver 15 for the user or the medical staff who can adjust the input parameters according to the information.

In summary, the medical electronic device has a detector, a processor, a transceiver and a function circuit. The processor can receive at least a control signal, which has been set by default externally, and instruct the function circuit to output an electrical stimulation signal to the electrode according to the control signal. Because the electrical stimulation signal carries the information about the default electrical stimulation frequency, the default electrical stimulation cycle and the default electrical stimulation intensity, the medical electronic device can turn itself on according to the electrical stimulation signal for electrical stimulation depending on the habitual behavior of the user or patient (for example: cycle days of pain). Therefore, it can avoid less effective treatment due to frequently electrically stimulating the affected nerve of the patient like the conventional manner.

Moreover, because the medical electronic device has the detector, the remaining battery of the battery module can be instantly detected by the detector so as to as effective as possible monitor the operation of the medical electronic device.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A medical electronic device, comprising:
at least one battery module;
a detector electrically connected to the at least one battery module, wherein the detector detects the remaining battery power of the at least one battery module and generates a detection signal;
a processor electrically connected to the detector to receive the detection signal, wherein the processor generates a first status information for user according to the detection signal;
a transceiver electrically connected to the processor and linked to an external control device with bidirectional wireless communication, wherein the processor transmits the first status information for user through the transceiver to the external control device with wireless communication, wherein the processor receives at least one control signal through the transceiver from the external control device with wireless communication; and
a function circuit electrically connected to the processor and at least one electrode, wherein the at least one electrode extends outward from the medical electronic device;
wherein, according to the at least one control signal, the processor controls the function circuit to output an electrical stimulation signal with default stimulation frequency, stimulation cycle and stimulation intensity to the at least one electrode, the voltage of the electrical stimulation signal ranges from −10V to −1V and from 1V to 10V, and the frequency of the electrical stimulation signal is between 200 KHz and 800 KHz.

2. The medical electronic device of claim 1, further comprising: a heat sensor electrically connected to the processor, wherein the heat sensor monitors a temperature of the medical electronic device and generates a sensor signal to the processor, wherein the processor generates a second status information according to the sensor signal.

3. The medical electronic device of claim 2, further comprising: an induction coil induced by an AC magnetic field caused by an external charging device; and a rectifier electrically connected to the induction coil and the at least one battery module to convert the current in the induction coil induced by the AC magnetic field into a DC current and transmit it to the at least one battery module, wherein the at least one battery module is rechargeable.

4. The medical electronic device of claim 3, wherein the external control device has a plurality of setup keys and at least one screen, the external control device sends the at least one control signal to the transceiver, and the processor receives the at least one control signal through the transceiver.

5. The medical electronic device of claim 2, wherein the external control device has a plurality of setup keys and at least one screen, the external control device sends the at least one control signal to the transceiver, and the processor receives the at least one control signal through the transceiver.

6. The medical electronic device of claim 2, wherein the voltage of the electrical stimulation signal ranges from −10V to −3V and from 3V to 10V.

7. The medical electronic device of claim 2, wherein the interval between the at least one electrode and at least one dorsal root ganglion of a human body is less than 2 cm to electrically stimulate the at least one dorsal root ganglion.

8. The medical electronic device of claim 1, wherein the at least one battery module is non-rechargeable.

9. The medical electronic device of claim 1, further comprising: an induction coil induced by an AC magnetic field caused by an external charging device; and a rectifier electrically connected to the induction coil and the at least one battery module to convert the current in the induction coil induced by the AC magnetic field into a DC current and transmit it to the at least one battery module, wherein the at least one battery module is rechargeable.

10. The medical electronic device of claim 9, wherein the external control device has a plurality of setup keys and at least one screen, the external control device sends the at least one control signal to the transceiver, and the processor receives the at least one control signal through the transceiver.

11. The medical electronic device of claim 1, wherein the external control device has a plurality of setup keys and at least one screen, the external control device sends the at least one control signal to the transceiver, and the processor receives the at least one control signal through the transceiver.

12. The medical electronic device of claim 1, wherein the voltage of the electrical stimulation signal ranges from −10V to −3V and from 3V to 10V.

13. The medical electronic device of claim 1, wherein the interval between the at least one electrode and at least one dorsal root ganglion of a human body is less than 2 cm to electrically stimulate the at least one dorsal root ganglion.

* * * * *